United States Patent [19]
Gordon et al.

[11] Patent Number: 4,696,743
[45] Date of Patent: Sep. 29, 1987

[54] CENTRIFUGATION

[75] Inventors: Alan J. Gordon, Liverpool; Donald G. Billington, Stoke on Trent, both of England

[73] Assignee: Shandon Southern Products Limited, Runcorn, England

[21] Appl. No.: 871,061

[22] Filed: Jun. 5, 1986

[51] Int. Cl.[4] .............................................. B01D 33/22
[52] U.S. Cl. ..................................... 210/361; 422/101
[58] Field of Search ............... 210/361, 781, 782, 541, 210/542; 422/101, 72, 73, 102

[56] References Cited
U.S. PATENT DOCUMENTS
4,391,710  7/1983  Gordon ............................... 210/361

*Primary Examiner*—Frank Sever
*Attorney, Agent, or Firm*—Vaden, Eickenroht, Thompson & Boulware

[57] ABSTRACT

Centrifugation apparatus comprising a sample chamber, a deposit-receiving surface such as a slide and a filter card having an aperture adapted to define on that surface a deposition area communicating with the sample chamber is characterized by the feature that liquid flow paths in the filter card from the perimeter of the aperture are selectively restricted in cross section so as to promote constant velocity flow of liquid, from the sample chamber into the card, in directions substantially normal to all points on the periphery of the aperture. This promotes uniform deposition of solids on the deposit-receiving surface throughout the deposition area, to facilitate inspection of the deposit and, particularly, automated optical scanning of the deposit. The cross sectional restrictions may be accomplished by local removal of filter card material; by local compression of the filter card; or by local impregnation of the card material with an occlusive agent.

10 Claims, 4 Drawing Figures

CENTRIFUGATION

FIELD OF THE INVENTION

This invention concerns the centrifugation of suspensions to effect separation of solids therefrom for, e.g., microscopic examination. The invention is especially concerned with the centrifugation of body fluid and like samples comprising cell suspensions to accomplish deposition of a cell layer on a slide or other receiving surface for cytological examination, a general objective of the invention being to facilitate and improve the preparation of such cell layers in routine cytological screening procedures, e.g., in the screening of cervical cell samples for carcinoma.

BACKGROUND TO THE INVENTION AND THE PRIOR ART

Thus it is known to place a cell suspension in a generally tubular sample chamber having an open end juxtaposed to the surface of a microscope or like slide, with the interposition of an apertured filter card that both provides a seal between the sample chamber and the slide surface and also serves to absorb the liquid components of the suspension. The assembly of sample chamber, slide and filter card is subjected to centrifugation to cause the deposition of a layer of cells on the slide surface and the removal of the suspension liquid into the filter card. One example of cytocentrifugation apparatus especially adapted to perform this cell separation and deposition technique is disclosed in U.S. Pat. No. 4,391,710. For an earlier example of such apparatus, see also G-I-T FACHZEITSCHRIFT FUR DAS LABORATORIUM, Vol. 5, No. 1 (January 1971), Darmstadt DE, at page 51, left-hand column.

As hitherto practised, for instance with the centrifugation apparatus of U.S. Pat. No. 4,391,710, the sample chamber is sized to deposit cells on a rather small, generally circular, area of the slide and handles correspondingly small samples of cell suspension. The rather small areas of cell deposit thereby produced are adequate for microscopic examination by a suitably trained operative making a visual examination but it is recognised that examination of the deposit would be facilitated if the deposit were spread over a larger area of the slide and, ideally, as a monolayer of cells. The uniform deposition of cells in a monolayer over a substantial area would, for instance, greatly facilitate counting of cells per unit area as well as the recognition of particular cell types of interest. Moreover, recent proposals for the automated examination of cell deposits by optical scanning devices require, for reproducibility of results, cells to be deposited in a monolayer over a, preferably rectangular, relatively large area of a suitable receiving surface such as a glass slide.

It should be understood that when a small volume sample of a suspension of solids in a liquid and contained in a circular section tube is centrifuged to deposit its suspended solids over a circular slide area defined by a correspondingly sized aperture in a significantly larger filter card, the liquid of the suspension tends to flow symmetrically and radially of the deposit area to be uniformly absorbed in the surrounding filter card. This flow of the liquid tends to carry some of the suspended solids away from the centre of the deposit area and towards the margin thereof, to lead to variations in thickness in the deposited layer, this tending to be thicker at its periphery than at its centre. Nonetheless, by appropriate choices of filter card absorbency and dimensions of the sample chamber, and by restricting the volume of liquid in the suspension sample, it is generally possible to obtain a deposit that is useful for visual examination, at least over the majority of its total area.

When, however, an attempt is made to cause the deposition over a non-circular surface area and, especially, over a relatively large non-circular area of the receiving surface, using samples containing larger volumes of suspending liquid, the flow of liquid transversely of the receiving surface and into the filter card is no longer symmetrical and tends to cause significant thickness variations in the deposited layer, rendering much of the area thereof difficult to examine reliably by visual methods and substantially useless for examination by automated optical scanning techniques.

Ideally, to achieve a uniform deposit thickness over the whole area of the deposited layer, the arrangement should be such that, under the artificial gravitational field created by centrifugation, solids (e.g. cells) suspended in the sample are caused to deposit on the receiving surface before there is any significant flow of the suspending liquid transversely of that surface and into the surrounding filter card, to cause lateral displacement of suspended solids before these are deposited. Moreover, the flow of suspending liquid into the surrounding filter card, when it occurs, should be slow to minimise the risk of currents over the deposited solids disturbing these and altering their disposition on the surface.

The ideal sequence of solids deposition followed by liquid removal is essentially unattainable in practice, some flow of suspension liquid into the filter card during deposition of the suspended solids being inevitable. However, the deposition perturbations due to transverse liquid flow can, we have discovered, be mitigated by suitable restriction of the rate of flow of liquid to the filter card and by ensuring that the flow pattern is such that at any point on the periphery of the deposit area, the local liquid flow is normal to the periphery and occurs at a substantially constant velocity. By observing these criteria, any flow-induced migration of suspended solids towards the periphery of the deposit area will be essentially uniform so that unacceptable thickening of the deposited layer will be confined to a substantially uniform width marginal band that can be ignored without difficulty in subsequent visual inspection and that can also be readily ignored by an automated optical scanning of the deposit area.

In filter card such as is used in the centrifugation procedures of interest, it can be shown that the volumetric flow rate of a liquid by capillary action in the card material is directly proportional to the cross-sectional area of the material in the flow path of the liquid. Accordingly the flow of liquid in a filter card from a particular region of the perimeter of an aperture therein can be restrained by restricting the flow cross-sectional area available in the card material for liquid flowing from that region of the aperture perimeter. This cross-sectional area restriction may be accomplished by physical removal of material, to form openings constituting liquid flow barriers therein as by cutting slots transverse to a liquid flow path to be restricted, by localised impregnation of the card with an occlusive, e.g. a hydrophobic, agent so as to inhibit liquid flow in the filter card region so impregnated, or by localised compression, as by clamping, of the card.

SUMMARY OF THE INVENTION

The present invention provides a centrifugation apparatus including a sample chamber, a deposit-receiving surface and a filter card apertured to define on that surface a deposition area communicating with said sample chamber, which apparatus is characterised by said filter card having liquid flow paths from the perimeter of said aperture of selectively restricted cross-sectional area to engender constant velocity flow of liquid from the sample chamber substantially normal to all points on the periphery of said aperture.

Preferably, the filter card aperture is rectangular and liquid flow paths in the filter card from the periphery of said aperture are selectively restricted in strip-like areas near and parallel with at least the intermediate regions of edges of the aperture.

The deposit-receiving surface is conveniently constituted by the surface of a slide, for instance a standard glass microscope slide (75 mm×25 mm) and the filter card is rectangular, having one dimension about 60 mm (i.e. corresponding to about 80% of the length of the slide) and its other dimension about 50 mm (i.e. approximating to twice the width of the slide) so that by folding the card may be wrapped around and overlie both faces of approximately 80% of the length of the slide. Such a card may be formed with a rectangular aperture the length of which is about 25 mm and the width of which is about 20 mm so as to be slightly less than the width (25 mm) of the slide and in a position to define a deposit-receiving area of corresponding shape nearer to one end of one face of the slide when the card is superimposed on the slide and folded and wrapped thereabout. The aperture in the card may be arranged symmetrically of the total area of the latter to simplify control of liquid flow in the card from the perimeter of the aperture therein. However, as such a symmetrical arrangement would require folding the card about two parallel lines to wrap it around the slide, an asymmetrical arrangement is preferred with the aperture located near to (e.g., about 2-3 mm from) one edge of the card so that by single folding of the card about its longer axis, it may be wrapped over one long edge of the slide with the card aperture appropriately positioned over one face of the slide. The tendency to asymmetric liquid flow in the card resulting from the asymmetrical location of the aperture therein may be compensated, in accordance with the invention, by suitably controlling the available liquid flow cross-sectional areas in the card adjacent to those edges of the aperture more remote from edges of the card.

Centrifugation apparatus in accordance with the invention is especially advantageous for use in conjunction with a sample chamber of the construction disclosed in our co-pending application Ser. No. 06/871,081 and/or for use in a cytocentrifuge of the construction disclosed in our co-pending application Ser. No. 06/871,530, both filed concurrently herewith.

DESCRIPTION OF PREFERRED EMBODIMENTS OF THE INVENTION

Figure 1:
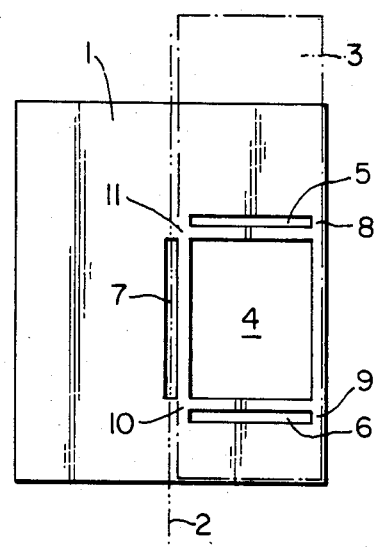
FIG. 1 is a plan view of one form of filter card having restricted liquid flow paths in accordance with the invention.

In the form of filter card shown in FIG. 1 of the drawings the filter card 1 is rectangular in shape, having a longer dimension about 60 mm and a shorter dimension about 50 mm. The longer axis of the card 1 is indicated at 2 while the outline of a standard glass microscope slide, 75 mm by 25 mm, is shown at 3 superimposed over one half of the card 1.

The card 1 is formed with a rectangular aperture 4 having a length of about 25 mm and a width of about 20 mm and symmetrically disposed within one half of the total width of the card 1 so as, as shown, to define on the slide 3 a correspondingly shaped deposit-receiving area, the longer edges of which are parallel to and equidistant from the long edges of the slide.

In accordance with the invention, the card 1 is also formed with liquid flow barriers, in this case in the form of three slots 5, 6, 7 parallel, respectively, with the upper and lower short edges of the aperture 4, and with the long edge of the aperture 4 adjacent to the long axis 2 of the card. The purpose of these slots is to restrict the cross-section available, in the card material, for flow of liquid from the perimeter of the aperture 4 into the main body of the card beyond the slots 5, 6 and 7: in this embodiment these slots form the only such flow path restrictions and effectively confine any flow of liquid from the perimeter of the aperture 4, to the card regions indicated at 8, 9, 10 and 11 respectively adjacent to the four corners of the aperture 4.

The unapertured half of the card 1, to the left of its axis 2 as seen in FIG. 1, constitutes a sump for liquid that in use enters the card at the perimeter of the aperture 4.

Figure 2:
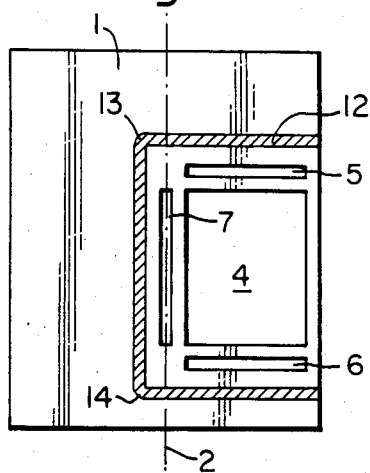
FIG. 2 is a plan view of another form of filter card having restricted liquid flow paths in accordance with the invention.

The form of card illustrated in FIG. 2 has features in common with that of FIG. 1 and these features are identified by corresponding reference numbers and will not be further described. However, in the filter card 1 shown in FIG. 2, liquid flow control is exercised additionally by restricting the cross-sectional area available for such flow, in the card material, by impregnating the card in a band 12 with an occlusive, e.g. a hydrophobic, material such as, for instance, a rubber.

For the purposes of illustration, the band 12 is shown as consisting of three linear legs respectively extending parallel with the slots 5, 6 and 7 and joined to one another to form a continuous band surrounding the aperture 4 and the slots 5, 6 and 7 and terminating at the right hand edge of the card 1 as seen in the drawing. However, it should be understood that the band 12 may have other shapes and may be interrupted to provide for precise control of liquid flow from particular regions of the perimeter of the aperture 4 into the main body of the filter card 1 external of the band.

Moreover, a suitably shaped band 12, continuous as shown or interrupted, for instance at the corner regions 13 and 14, may be used to control liquid flow in a filter card from which one or more of the slots 5, 6 and 7 has been omitted.

The band 12 may conveniently be formed by a printing-like operation, the chosen occlusive or hydrophobic material (e.g. a solution of a rubber in a suitable solvent)

being imprinted on or applied to the card using, for instance, a stencil.

The liquid flow barrier constituted as above described by a slot such as one of the slots 5, 6, 7, or by impregnation with an occlusive material in a band or region such as the band 12, may alternatively be provided by local compression of the card material to reduce the available cross section for liquid flow in the card material. Such localised compression could be achieved by clamping the card against the slide 3 or other deposit-receiving member with the use of pressure members, such as ribs on a holder for the card and slide assembly, disposed engage the card and indent it in the regions requiring localised compression.

A filter card such as has been described with reference to FIGS. 1 and 2 is intended to be used in conjunction with a suitable sample chamber that is assembled with the card and a suitable deposit-receiving surface such as that of a microscope slide 3, and so fitted to a centrifuge head that the artificial gravitational field produced by operation of the centrifuge acts normal to the deposit-receiving surface to accomplish controlled deposition of solids from a suspension contained in the sample chamber. The apertured filter card with its restricted liquid flow paths from the aperture therein may be used with any design of sample chamber capable of making up the required assembly with the card and deposit-receiving surface or slide and, for example, a sample chamber having a configuration generally similar to that disclosed in U.S. Pat. No. 4,391,710 might be employed.

However, such a filter card is most conveniently employed in conjunction with a sample chamber of the construction disclosed in our copending application Ser. No. 06/871,081 and FIGS. 3 and 4 illustrate such a sample chamber.

Figure 3:
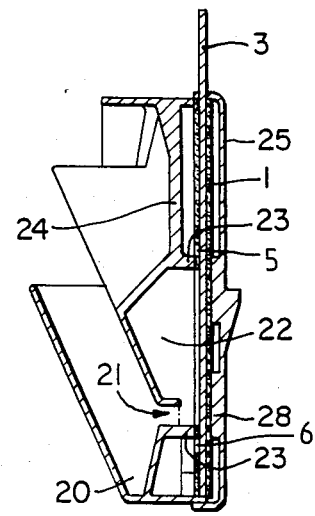
FIG. 3 is a sectional view of a sample chamber with which the filter card of FIG. 1 or FIG. 2 may be used showing a slide and filter card installed therein.

FIG. 3 is a longitudinal section of the sample chamber, and also shows a filter card 1 and slide 3 installed therein. The sample chamber is a moulding in a suitable plastics material and includes a sample reservoir 20 communicating via a slot 21 with a deposition chamber 22 that is rectangular in cross-section with a longer dimension—vertically as seen in FIG. 3—of about 25 mm and a shorter dimension of about 20 mm, the deposition chamber 22 terminating in a narrow rectangular aperture-defining wall 23 that projects as a rib on the rear surface of the main body part 24 of the sample chamber.

Figure 4:
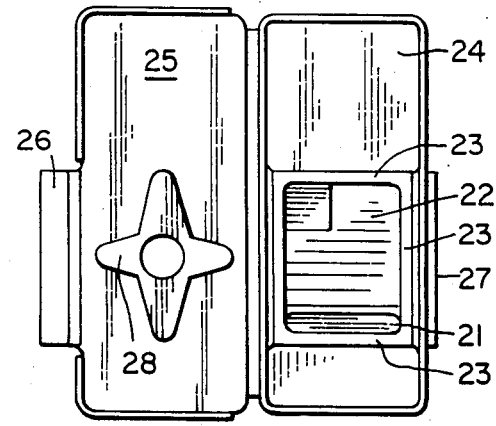
FIG. 4 is a rear view of the sample chamber of FIG. 3, showing the rear door thereof in its open condition.

The sample chamber is formed with an integrally hinged rear door 25, shown in its open condition in FIG. 4, with a latch 26 that in the closed condition of the door engages over a series of dog teeth 27 on the body 24. The internal face of the door 25 is formed with a cruciform pressure pad 28.

In use, a filter card of the configuration and dimensions illustrated in FIG. 1 or FIG. 2 is fitted to the sample chamber so that its aperture 4 registers with the deposit chamber 22, the card at the margin of the aperture 4 therein engaging the end surface of the wall 23. For convenience of assembly and use, the card is conveniently secured in place in the sample chamber as by ultrasonic welding to the pressure pad 28, to form a one-use, disposable, unit, perhaps supplied in a sterile pack.

The sample chamber of FIGS. 3 and 4 is intended to be used with standard microscope slides such as the slide 3 depicted in FIG. 1 and in use such a slide is placed over the apertured half of the card 1—as in FIG. 1—that in turn has been placed or fixed in position relatively to the deposition chamber of the sample chamber. The card is folded about its axis 2 so as to become wrapped about the slide with the unapertured area of the card lying against the face of the slide remote from the deposit chamber 22. Conveniently this folding of the card is accomplished simply by closing the rear door 25 of the sample chamber, whereby the pressure pad 28 holds the slide firmly against the wall 23 without, however, placing more than a small proportion of the total area of the filter card (the region trapped between the slide and the wall 23 on the front of the slide, and the region trapped between the slide and the pressure pad 28 at the rear of the slide) under such pressure as would diminish the capability of the card to absorb liquid, or interfere with flow of liquid in sump-constituting areas of the card. As shown in FIG. 3, the slots 5 and 6 in the card lie just outboard of the wall 23.

As more fully explained in our aforesaid co-pending Applications the assembly of sample chamber with filter card and slide is intended to be fitted to a complementary bucket on the head of a centrifuge, to enable centrifugation of a suspension sample placed in the sample reservoir 20, the sample being transferred from this reservoir through the slot 21 to the deposition chamber 22 by the artificial gravitational field produced when the centrifuge is run up.

We claim:

1. In centrifugation apparatus including a sample chamber, a deposit-receiving surface and a filter card apertured to define on that surface a solids deposition area communicating with said sample chamber, the improvement that comprises said filter card having liquid flow paths from the perimeter of its said aperture of selectively restricted cross-sectional area for engendering substantially constant velocity flow of liquid from the sample chamber substantially normal to all points on the periphery of said aperture sufficient for promoting substantially uniform deposition of said solids on said surface throughout said deposition area to facilitate inspection of said deposition.

2. The apparatus of claim 1, in which the said filter card aperture is rectangular and liquid flow paths in the filter card from the periphery of said aperture are selectively restricted in strip-like areas near and parallel with at least the intermediate regions of edges of the aperture.

3. The apparatus of claim 2, in which the said deposit-receiving surface is constituted by the surface of a slide and said filter card is rectangular, having dimensions such that by folding the card may be wrapped around and overlie at least part of the length of both faces of the slide.

4. The apparatus of claim 3, in which the filter card dimensions are such that by folding it may be wrapped around and overlie both faces of about 80% of the length of the slide.

5. The apparatus of claim 4, in which the filter card aperture has dimensions to define a deposit-receiving area slightly less in width than the slide.

6. The apparatus of claim 3, in which the filter card aperture is disposed near to one edge thereof to enable single folding of the card to provide for wrapping of the card over one edge of the slide with positioning of the card aperture over one face of the slide.

7. The apparatus of claim 2, in which said filter card has liquid flow barrier openings comprising slots in said strip-like areas of the filter card.

8. The apparatus of claim 1, in which said filter card has openings constituting liquid flow barriers therein.

9. The apparatus of claim 1, in which said filter card is locally impregnated with an occlusive agent to inhibit flow of liquid in a filter card region providing a liquid flow path from the deposition area-defining aperture.

10. The apparatus of claim 1, in which said filter card is locally compressed to restrict the card cross section available for liquid flow from said deposition area-defining aperture in the card.

* * * * *